(12) United States Patent
Lea et al.

(10) Patent No.: US 10,119,973 B2
(45) Date of Patent: Nov. 6, 2018

(54) ANALYTE QUANTIFICATION MULTIPLEX MICROARRAYS COMBINING INTERNAL AND EXTERNAL CALIBRATION

(75) Inventors: Peter Lea, Toronto (CA); Jennifer Hansen, Toronto (CA); Kate Smith, Toronto (CA)

(73) Assignee: SQI DIAGNOSTICS SYSTEMS INC., Toronto, ON (CA)

( * ) Notice: Subject to any disclaimer, the term of this patent is extended or adjusted under 35 U.S.C. 154(b) by 807 days.

(21) Appl. No.: 13/504,748

(22) PCT Filed: Oct. 29, 2010

(86) PCT No.: PCT/CA2010/001698
§ 371 (c)(1),
(2), (4) Date: Jul. 19, 2012

(87) PCT Pub. No.: WO2011/050463
PCT Pub. Date: May 5, 2011

(65) Prior Publication Data
US 2012/0283122 A1 Nov. 8, 2012

(30) Foreign Application Priority Data

Oct. 30, 2009 (CA) .................................. 2684636

(51) Int. Cl.
*C12Q 1/68* (2018.01)
*G01N 33/68* (2006.01)

(52) U.S. Cl.
CPC ..... *G01N 33/6845* (2013.01); *G01N 2440/18* (2013.01); *G01N 2800/101* (2013.01); *G01N 2800/52* (2013.01)

(58) Field of Classification Search
None
See application file for complete search history.

(56) References Cited

U.S. PATENT DOCUMENTS

| 6,916,621 | B2* | 7/2005 | Shah | C12Q 1/6809 |
| | | | | 435/174 |
| 2006/0204968 | A1* | 9/2006 | Haeupl et al. | 435/6 |
| 2007/0111246 | A1* | 5/2007 | Carrick et al. | 435/6 |

FOREIGN PATENT DOCUMENTS

| JP | 2004-226415 A | 8/2004 |
| JP | 2005-114532 A | 4/2005 |
| JP | 2007-010488 A | 1/2007 |
| JP | 2007-505326 A | 3/2007 |
| JP | 2008-506956 A | 3/2008 |

(Continued)

OTHER PUBLICATIONS

Hartmann et al, Anal Bioanal Chem, 2009, 393:1407-1416.*

(Continued)

*Primary Examiner* — Robert T. Crow
(74) *Attorney, Agent, or Firm* — Pepper Hamilton LLP

(57) ABSTRACT

The present invention relates to multiplex microarrays and methods for the quantification of analytes. In particular, the invention relates to improved methods which standardize a target analyte concentration in a test sample against a reference standardization curve derived from validated, approved and recognized reference standards for the target analyte of known concentrations. The present invention also relates to methods and checks for simultaneous measurement of confidence confirming normalization standards and controls.

9 Claims, 6 Drawing Sheets

(56) References Cited

FOREIGN PATENT DOCUMENTS

| JP | 2009-515531 A | 4/2009 |
|---|---|---|
| WO | WO 2006/007726 A1 | 1/2006 |
| WO | WO 2009/103988 | 8/2009 |
| WO | WO 2010/075632 A1 | 7/2010 |

OTHER PUBLICATIONS

Rodriguez et al, Journal of Chromatograpy A, 1158, (2007), p. 33-46.*

Fu et al. "Comparison of Multiplex Immunoassay Platforms" Feb. 2010, *Clin. Chem.* 56(2):314-318.

International Search Report dated Feb. 17, 2012 from PCT/CA2010/001698.

Lea et al. "Automated quantitative microarray assay platforms; A microarray-based assay platform has been developed for high test throughput, with a fully automated protocol" Nov. 1, 2009, *IVD Technology*, 15(9):43-49.

Lea et al. "Advantages of Multiplex Proteomics in Clinical Immunology: The Case of Rheumatoid Arthritis: Novel IgXPLEX™ Planar Microarray Diagnosis" Dec. 9, 2009, *Clinic Rev. Allerg. Immunol.* 37(3).

Ling et al. "Multiplexing Molecular Diagnostics and Immunoassays Using Emerging Microarray Technologies" Jan. 2007, *Expert Rev. Mol. Diagn.* 7(1):87-98.

European Supplemental Search Report and Written Opinion dated Apr. 11, 2013 for EP 10825894.

Feng et al. "Parallel Detection of Autoantibodies with Microarrays in Rheumatoid Diseases" Feb. 1, 2004, Clin. Chem. 50(2):416-422.

SQI Diagnostics 510(K) Summary, Section 8, Oct. 29, 2009.

SQI Diagnostics Systems "IGX Plex Rheumatoid Arthritis (RA) Assay and SQIDWORKS Diagnostic Platform" Oct. 29, 2009, Retrieved from the Internet: URL:http://www.accessdata.fda.gov/cdrh_docs/pdf8/K083080.pdf.

Biessels "A Novel Anti-Citrullinated Peptide Antibody Assay Using a Four-Analyte Multiplexed QuantiSpot™ Rheumatoid Arthritis Test System" Apr. 1, 2008, Poster Presentation at 40th Oak Ridge Conference.

Biessels et al. "Specificity and Sensitivity of a Novel Anti-citrullinated Peptide Antibody Assay in a Four-analyte Multiplexed Quantispot™ Rheumatoid Arthritis Test System" Nov. 1, 2008, 40th Oak Ridge Conference 54:1934 (Poster 4).

Davis et al. "Principles of Curve Fitting for Multiplex Sandwich Immunoassays" Jan. 1, 2007, Bio-Plex Suspension Array System, pp. 1-4.

Cuadros-Rodriguez et al. "Principles of Analytical Calibration/Quantification for the Separation Sciences" 2007, J Chromatogr A, 2007, vol. 1158, No. 1-2, p. 33-46.

* cited by examiner

ANALYTE QUANTIFICATION MULTIPLEX MICROARRAYS COMBINING INTERNAL AND EXTERNAL CALIBRATION

FIELD OF THE INVENTION

The present invention relates to multiplex microarrays and methods for the quantification of analytes, in particular, the invention relates to improved methods which standardize analyte concentrations against an internal reference standardization curve and a standardization curve obtained from known reference standards. The present invention also relates to methods and checks for simultaneous measurement of confidence confirming normalization standards and controls.

BACKGROUND OF THE INVENTION

A biomarker is a characteristic that may be measured and evaluated as an indicator of the biological state of an organism. In medicine, a biomarker may be an exogenous substance that is introduced into a patient to examine biological processes, such as organ function, and biochemical functions and pathways. A biomarker may also be a biomolecule obtained from a patient, such as a protein or a nucleic acid, that indicates a particular disease state or response to a drug therapy. Such biochemical biomarkers are also particularly useful in the discovery and development of new drugs. During early phase clinical research of such drugs, quantification of suitable biomarkers may potentially aid researchers in more rapid identification of the most promising drug candidates, thus streamlining the drug development process. Disease-related biomarkers may also be used for diagnosis or prognosis of disease, and as a measure of therapeutic efficacy. Thus, it is of great importance to identify and validate new biomarkers that may be of use in assessing patient health and/or response to therapeutic interventions, as well as provide a method for accurate and reproducible determination of known biomarkers.

Biomarker analysis is highly dependent on the integrity of reagents such as antibodies, which are themselves derived from biologic sources and thus may be subject to issues of quality control and stability. In many biomarker assay processes, non-certified standards, such as recombinant proteins and surrogate matrices have been used, in order to derive a calibration curve. Thus, parallel studies need to be performed where the response of the assay to a range of calibration standard concentrations made up in the surrogate matrices is comparable to that of a series of dilutions of patient samples. Dilution linearity can also be problematic, as antibody and ligand-binding affinities can vary significantly in different media. The goal of biomarker assay development and qualification is to develop assays for clinical benefit.

Immunoassays such as the Enzyme Linked Immunosorbent Assay ("ELISA"), based on the binding specificity of antibodies for a target antigen, are well-known in the art (see for example, Engvall et al., *Immunochem.* 1971, 8:871; Ljunggren et al., *J. Immuno. Meth.* 1987, 88:104; Kemeny et al., *Immunol. Today* 1986, 7:67). Immunoassays are highly useful for identifying new biochemical biomarkers such as proteins or nucleic acids, as well as quantifying known biomarkers, as antibodies can be generated against a specific biomarker.

Examples of methods of quantitative determination of biomarkers via immunoassays are known in the art. See for example, Hawkes et al., *Anal. Biochem.* 1982, 119:142-147, and Tobin and Gordon, *J. Immunol. Methods* 1984, 72:313-340, and U.S. Pat. No. 5,486,452 to Gordon et al., entitled "Device and kits for immunological analysis".

Previously employed immunoassay methods tended to be limited as they could only detect one target analyte per test cycle, within a single reaction vessel. Attempts have been made to decrease the time for completion of each test cycle, and to increase the number of tests that are carried out per cycle, by adhering probe molecules (e.g. antibodies) to a solid substrate (e.g. a bead or a well on a plate), and then washing test samples, buffers, and reagent solutions over the solid substrate.

A microarray is a device in which a large number (e.g. hundreds to thousands) of samples of biomolecules, such as DNA and proteins, are affixed or immobilized to a suitable non-reactive substrate surface, such as plastic (e.g. polypropylene, polystyrene, cyclo-olefins), silicone, and glass. If the substrate surface is relatively flat, the biomolecules may be "printed" on the surface, whereby printing is carried out by application of a known volume of a "spotting" buffer containing a known concentration of the biomolecule. With the biomolecules fixed to a known substrate or known locations on a substrate surface, the substrate surface may then be exposed to biochemical/chemical reagents for the purposes of detection, and qualitative and quantitative analysis. For example, a microarray may be used to carry out an ELISA-type immunoassay, wherein the biomolecule affixed to the substrate is an antibody, and the substrate surface is then exposed to a test solution containing an antigen to which the antibody can bind. The substrate surface can then be washed with a buffer solution and exposed to a secondary antibody which is conjugated to either a detectable label (e.g. a radiolabel or a fluorescent dye) or an enzyme which catalyzes a reaction for which the reaction product is coloured and thus detectable. The microarray thus allows high throughput analysis of large quantities of samples. At the same time, computer software programs have been developed to analyse the large quantities of data that are generated from a microarray.

A number of examples of microarrays and methods of handling the data provided by microarrays are known in the art. See for example, U.S. Pat. No. 6,516,276 to Ghandour et al., entitled "Method and apparatus for analysis of data from biomolecular arrays", U.S. Pat. No. 6,916,621 to by Shah, entitled "Methods for array-based comparative binding assays", and U.S. Pat. No. 7,072,806 to Minor, entitled "Methods and systems for comparing data values across multiple platforms".

It is typical for several antigenic substances or biomarkers to be associated with the detection and diagnosis of a biological process, including diseases. To confirm the presence of multiple biomarkers, each marker within a test sample would require a separate immunoassay to be carried out. This greatly increases the amount of time to analyse a given test sample, and gives rise to other problems, such as increased cost and increased experimental errors which increase with every assay that must be carried out. Thus, it is desirable to identify and employ methods of quantitative determination of biomarkers that allow detection and quantitative measurement of multiple antigens or biomarkers simultaneously, i.e. "multiplex" detection and determinations.

As a microarray allows simultaneous, multiple biochemical analyses, microarrays may be adapted to perform multiplex analyte detection. In order to increase the capacity of existing microarrays, "multiplex" microarrays have been developed, wherein multiple different probe biomolecules are present in the same microarray. This allows users to detect and analyse more than one target analyte in a test sample. This is particularly useful for high-throughput screening of tissue/body fluid samples for multiple biomarkers that may be used for detection and diagnosis of biological processes including pathogenic and physiological disorders.

There are a number of problems that may arise during microassays, including difficulties in obtaining accurate quantitative analyses and reproducibility. Such problems tend to be magnified in attempts to carry out multiplex detections. Cross-hybridization may occur between biomolecules that have been fixed to the surface of the microarray. In addition, not all the desired amount of biomolecule may adhere to the substrate surface during the printing process. For example, in the case of a relatively flat substrate surface, there may be an uneven printing of the amounts of biomolecule on the substrate surface, which would affect accuracy in quantitative analyses. Furthermore, during the course of an assay, unknown amounts of the biomolecules may be washed away during the application and removal of assay reagents. Thus, the actual amount of the biomolecule within a given location on a substrate surface during the course of the assay may be less than the theoretical printed amount, i.e. the amount calculated based on the known concentration of the spotting buffer and the volume of spotting buffer applied to the surface. However, prior art methods for quantifying analyte amounts in a test sample do not take into account the discrepancies between the theoretical amounts and the actual amounts of the biomolecule immobilized on the microarray.

Accordingly, there is a need to develop a method to normalize the data obtained from a microarray to minimize the experimental errors inherent to the microassay method, such as may be due to discrepancies between the theoretical concentration of a biomolecule on the microarray substrate surface, based on the concentration of the coating/spotting buffer, and the actual concentration of the biomolecule that exists on the substrate surface. In addition, as a single test cycle of a multiplex microarray may provide data from multiple assays or batches of standards, there is a need for a method to compare multiple assays or batches of standards to enable conversion values between different assays or standards and to provide a reference basis across all such assays.

SUMMARY OF INVENTION

In accordance with abroad aspect of the present invention, there is provided a method for quantifying one or more analyte(s) in a test sample comprising:
(a) providing a plurality of discrete reaction substrates, each reaction vessel having a microarray printed thereon, said microarray comprising:
a calibration matrix comprising a plurality of calibration spots, each calibration spot comprising a predetermined amount of a calibration compound, wherein each calibration spot corresponds to a theoretical concentration of the calibration compound; and
an analyte capture matrix comprising a plurality of capture spots, each capture spot comprising a predetermined amount of an agent which selectively binds to said analyte;
(b) applying a predetermined volume of the test sample to one of said discrete reaction substrates;
(c) providing a plurality of reference standards each having a known concentration and each comprising a predetermined amount of each of said analyte;
(d) applying a predetermined volume of each reference standard to one of said discrete reaction substrates;
(e) on each discrete reaction substrate from step (b) and step (d):
(i) applying a labelled reporter compound, wherein said labelled reporter compound provides a measurable signal intensity that is directly proportional to the amount of analyte or calibration compound bound to each spot;
(ii) measuring a signal intensity value for each spot within the microarray;
(iii) generating a first calibration curve for the reaction substrate of step (b), and generating a second calibration curve for the reaction substrate of step (d), in each case said calibration curve being prepared by fitting a curve to a graph of the signal intensity values versus the theoretical concentrations of the calibration compound;
(iv) determining a first analyte equivalent concentration of the test sample, using the first calibration curve, and determining a second analyte equivalent concentration of each of the reference standards, using the second calibration curve;
(f) generating a reference standardization curve by fitting a curve to a graph of the second analyte equivalent concentration versus the known concentration of each of the reference standards; and
(g) normalizing the first analyte equivalent concentration of the test sample using the reference standardization curve to obtain a corrected analyte concentration.

In an embodiment of the method as provided above, in step (e(iii)), the first and second calibration curves are generated by:
(1) in the calibration matrix, if the calibration matrix comprises two or more calibration spots that are replicates corresponding to a common theoretical concentration of the calibration compound, normalizing the measured signal intensity value for each of the replicate calibration spots to a mean measured signal intensity value for each of said calibration spots; and
(2) fitting a curve to a graph of the mean measured signal intensity values for each of said calibration spots versus each of the corresponding theoretical concentrations of the calibration standard.

In a further embodiment of the method as provided above, in step (e(iv)), the concentration of the analyte in the test sample or the reference standard is determined by:
(3) in the analyte capture matrix of each of the reaction substrates of step (b) and of step (d), if the analyte capture matrix comprises two or more capture spots that are replicates, normalizing the measured signal intensity value for each of the replicate capture spots to a mean measured signal intensity value and normalizing the measured signal intensity value for each of the spots to a mean measured signal intensity value for each of said capture spots; and
(4) (i) calculating the concentration of the analyte in said test sample, using the mean measured signal intensity value for each of said capture spots of the reaction substrate of step (b) and the first calibration curve; and
(ii) calculating the concentration of the analyte in each said reference standards, using the mean measured signal intensity values for each of said capture spots of the reaction substrate of step (d) and the second calibration curve.

The normalization of the measured signal intensity value for each of the spots of calibration matrix and the sample capture matrix may be performed by applying the Tukey Biweight algorithm.

In an embodiment of the method of the invention, the total number of the spots of the analyte capture matrix is at least equal to the total number of spots of the calibration matrix. In a further embodiment of the method, there are between 3 to 20 different theoretical concentrations of the analyte(s), corresponding to a linear dilution series. In yet another embodiment of the method, there are between 3 to 15 spots for each of the theoretical concentrations of the calibration standard.

In an embodiment of the invention, the labelled reporter compound is a fluorescently labelled antibody.

In another embodiment of the invention, the plurality of reaction substrates is in the form of a multi-well assay plate. In yet another embodiment of the invention, the plurality of reaction substrates is in the form of a plurality of beads.

In another embodiment of the invention, the test sample is a biological sample.

In another aspect of the invention, there is provided a use of the method according to any of the above-noted embodiments, wherein the biological sample is obtained from a patient, and the use comprises any one of the following:
(a) monitoring the progress of a disease in said patient;
(b) measuring an effect of a treatment on said disease; and
(c) measuring a concentration of a drug in said patient during said treatment of said disease;
wherein the one or more analytes to be quantified is/are biomarker(s) indicative of said disease.

In yet another aspect of the invention, there is provided a use of the method according to the above-noted embodiments, for diagnosing rheumatoid arthritis in a subject, comprising:
(1) measuring in a biological sample obtained from said subject:
   the concentration levels of each of rheumatoid factor-IgA, rheumatoid factor-IgG, and rheumatoid factor-IgM; and
   at least one anti-cyclic citrullinated peptide antibody selected from the group consisting of anti-cyclic citrullinated peptide-IgG, anti-cyclic citrullinated peptide-IgA, and anti-cyclic citrullinated peptide-IgM,
   wherein a reference standard of known concentration for each of rheumatoid factor-IgA, rheumatoid factor IgG and rheumatoid-IgM and the at least one selected anti-cyclic citrullinated peptide antibody is provided; and
(2) (i) comparing the measured concentration levels of each of rheumatoid factor-IgA, rheumatoid factor-IgG, and rheumatoid factor-IgM, with corresponding index normal levels of rheumatoid factor-IgA, rheumatoid factor-IgG, rheumatoid factor-IgM; and
   (ii) comparing the measured concentration levels of the selected anti-cyclic citrullinated peptide antibody/antibodies with corresponding index normal levels of the selected anti-cyclic citrullinated peptide antibody/antibodies,
wherein any of the measured concentrations levels of the above-noted biomakers which exceed index normal levels is diagnostic for rheumatoid arthritis.

In yet another aspect of the invention, there is provided a use of the method according to the above-noted embodiments, for monitoring rheumatoid arthritis treatment in a subject suffering therefrom, comprising measuring the concentration levels of: rheumatoid factor-IgA, rheumatoid factor-IgG, rheumatoid factor-IgM and at least one anti-cyclic citrullinated antibody selected from the group consisting of anti-cyclic citrullinated peptide-IgG, anti-cyclic citrullinated peptide-IgA, and anti-cyclic citrullinated peptide-IgM. The measurement of the concentration levels of the above-noted biomarkers is carried out a plurality of times during the treatment.

In an embodiment of the above-noted use of the method, for diagnosing rheumatoid arthritis and/or monitoring rheumatoid arthritis treatment, the microarray comprises a calibration matrix comprising a plurality of spots comprising a predetermined amount of a calibration compound, each spot corresponding to a theoretical concentration of the calibration compound; a first analyte capture matrix comprising a plurality of spots comprising a predetermined amount of rheumatoid factor; and a second analyte capture matrix comprising a plurality of spots comprising a predetermined amount of cyclic citrullinated peptide.

In yet another embodiment of the above-noted use of the method, for diagnosing rheumatoid arthritis and/or monitoring rheumatoid arthritis treatment, the microarray further comprises one or more of the following:
(i) a positive control matrix comprising a plurality of spots comprising a predetermined amount of IgA or fragments thereof, a predetermined amount of IgG or fragments thereof, and a predetermined amount of IgM or fragments thereof;
(ii) a negative control matrix comprising a plurality of spots which is free of:
   any compound which interacts with a labelled reporter compound;
   any compound which selectively binds to any one of the following selected from the group consisting of rheumatoid factor-IgA, rheumatoid factor-IgG, rheumatoid factor-IgM; and any compound which selectively binds to any one of the following selected from the group consisting of anti-cyclic citrullinated peptide-IgG, anti-cyclic citrullinated peptide-IgA, and anti-cyclic citrullinated peptide-IgM; and
(iii) a sample control matrix comprising a plurality of spots comprising an agent which selectively binds an analyte associated with the biological sample, wherein said analyte is a compound naturally occurring in the biological sample or a foreign compound added to the biological sample; with the proviso that the analyte is not rheumatoid factor-IgA, rheumatoid factor-IgG, rheumatoid factor-IgM, anti-cyclic citrullinated peptide-IgG, anti-cyclic citrullinated peptide-IgA, or anti-cyclic citrullinated peptide-IgM.

When using the method of the invention according to the above-noted embodiments to diagnose or treat rheumatoid arthritis, the method may be carried out on a multi-well assay plate, wherein a well of the assay plate comprises a microarray as described above, and wherein the multi-well assay plate comprises one or more confidence confirmation normalization standards and controls. Alternatively, the method may be carried out on a plurality of beads, wherein an individual bead comprises a microarray as described above, and wherein the plurality of beads comprises one or more confidence confirmation normalization standards and controls.

In a further embodiment of the above-noted use of the method, for diagnosing rheumatoid arthritis and/or monitoring rheumatoid arthritis treatment, the plurality of reaction substrates (which may be either one or more individual wells of the above-noted multi-well assay place, or one or more beads of the above-noted plurality of beads) may further comprise one or more of the following controls:

- at least one positive control for each of rheumatoid factor-IgA; rheumatoid factor-IgG; rheumatoid factor-IgM; and at least one positive control for said selected anti-cyclic citrullinated peptide(s);
- at least one negative control for each of rheumatoid factor-IgA; rheumatoid factor-IgG; rheumatoid factor-IgM; and at least one negative control for said selected anti-cyclic citrullinated peptide(s);
- at least one positive control for each of the reference standards for rheumatoid factor-IgA, rheumatoid factor-IgG, and rheumatoid factor-IgM; and at least one positive control for each of the reference standards for said selected anti-cyclic citrullinated peptide(s);
- one or more configuration controls for confirming matrix location, matrix rotation, matrix shift, and number of spots per array;
- one or more replicate controls for confirming replicate signal intensity;
- one or more process controls for serum confirmation; background signal and liquid volume transfer confirmations;
- one or more configuration controls for confirming internal calibration curves; and
- one or more configuration controls for confirming standardization curves.

An advantage of the present invention is that it provides an improved microarray based method for quantifying the amount of a target analyte in a test sample which corrects for these inherent discrepancies in the amount of the applied probe and calibration standard. The method may be used to measure one or more analytes in a test sample in a single reaction vessel. The method is particularly useful for accurately quantifying the amounts of multiple target analytes in a test sample, using multiplex microarrays.

Yet another advantage of the invention is that it provides a method to more accurately quantify clinically relevant biomarkers in biological samples for diagnostic or prognostic purposes. The method disclosed herein may also be used to more accurately monitor the progress of a disease and also the effect of a treatment on a disease.

Other and further advantages and features of the invention will be apparent to those skilled in the art from the following detailed description of an embodiment thereof, taken in conjunction with the accompanying drawings.

BRIEF DESCRIPTION OF THE DRAWINGS

The present invention will be further understood from the following detailed description of an embodiment of the invention, with reference to the drawings in which.

DETAILED DESCRIPTION OF EMBODIMENTS

Figure 1:
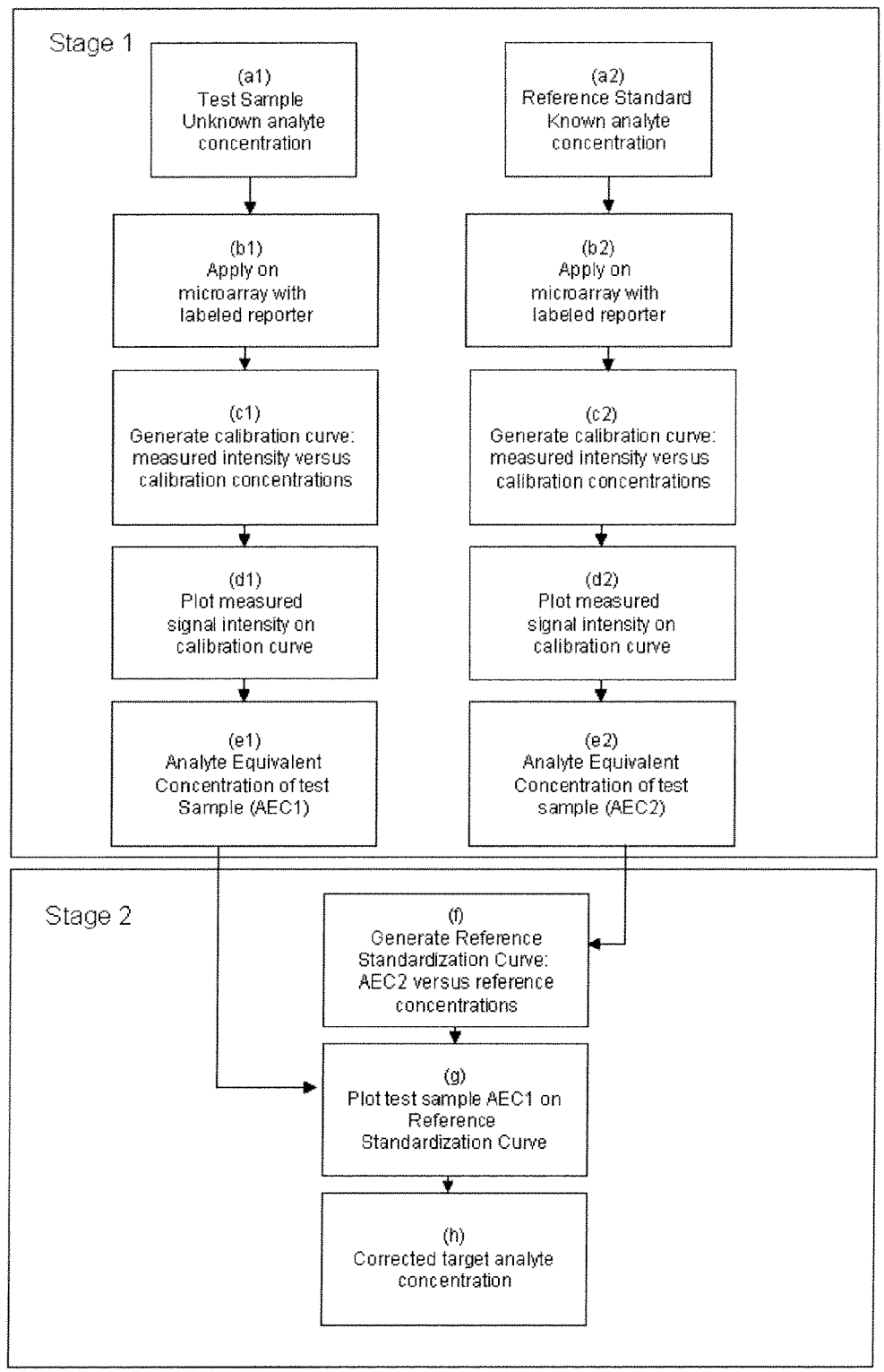
FIG. 1 is a flow chart illustrating the initial calibration and reference standardization steps for performing a multiplex assay

The use of microarrays for the detection and quantification of target analytes in a test sample, such as a biological sample obtained from a patient, is well known. The process for quantifying the amount of a target analyte in the test sample typically involves providing a microarray comprising an agent (also referred to as a "probe") which selectively binds to the target analyte, wherein the probe is first immobilized onto a solid surface of the microarray (also referred to as the "substrate"). Where the substrate is a relatively flat surface, such as the base of a well of a multi-well assay plate (also referred to as a "microtitre plate" or "microplate"), the probe may be immobilized onto the surface of the microarray by preparing a spotting solution comprising a known concentration of the probe and printing a predetermined volume of the spotting buffer onto the surface to provide capture spots (also referred to as "test dots") which will bind the target analyte, if present, in the test sample. Similarly, where the substrate is a spherical surface, such as may be found on beads that are commonly used for biochemical analyses, the probe may be immobilized onto the surface of the bead by preparing a coating solution comprising a known concentration of the probe, and immersing the bead(s) in the coating solution.

Calibration standards of known concentration of the target analyte can be used for the purpose of constructing a calibration curve. The calibration standard may also be a surrogate compound with similar biochemical characteristics to the target analyte. In an example where the substrate surface is relatively flat, the calibration standards may be applied to the microarray in the same manner as the capture spot containing the probe for the target analyte, to form "calibration spots". Thus, the microarray may comprise a plurality of calibration spots, each of which include a predetermined amount of the target analyte or surrogate compound, immobilized on the substrate surface of the microarray. A reporting system is provided which detects the amount of analyte bound to the microarray. For example, a commonly used reporting system is a fluorescently labelled antibody which selectively binds to the analyte. A calibration curve is generated by fitting a curve to a graph of the measured signal intensity of the labelled reporter for the calibrations spots (y axis) versus the theoretical concentrations of the calibration standards (x axis). Fitting the curve to the graph may be done by well-known mathematical and statistical methods, such as linear regression. The calibration curve is then used to determine the concentration of the analyte in the test samples based on measured signal intensities for the capture spots, wherein the measured signal intensities of the capture spots, taken as y values, are plotted on the calibration curve, and the corresponding x value is taken as the concentration of the analyte in the test samples.

Typically, during the printing process, not all of the probe and the calibration standard will adhere to the substrate surface of the microarray. Furthermore, during the course of an assay, small and unknown amounts of the probe and the calibration standard may be washed away during the application and removal of assay reagents. Thus, the actual amount of the probe or calibration standard immobilized on the surface during the course of the assay is less than the theoretical printed amount, i.e. the amount calculated based on the known concentration of the probe or the calibration standard in their respective spotting buffer and the volume of spotting buffer applied to the surface. However, prior art methods for quantifying analyte amounts in a test sample do not take into account the discrepancies between the theoretical amounts and the actual amounts of the probe and the calibration standard immobilized on the microarray.

There is now provided an improved microarray-based method for quantifying the amount of a target analyte in a test sample which corrects for these inherent discrepancies in the amount of the applied probe and calibration standard. The method may also be used in a multiplex microarray, to measure more than one target analyte in a test sample in a single reaction vessel.

Referring to FIG. 1, an embodiment of the method of the invention may be understood according to the following description.

The method comprises two stages as illustrated in FIG. 1 ("FIG. 1").

In order to carry out the method as described below, there is provided a plurality of discrete reaction substrates, each having a microarray printed thereon. The microarray can be fixed, by printing or coating, on the surface of each of the reaction substrates using conventional methods that are well-known in the art. In the present embodiment, it is assumed that the reaction substrate is a flat surface such as provided by the base of a well of a multi-well assay plate. However, it is understood that other types of reaction substrates, such as beads, may be used. As used herein, the term "microarray" refers to series of discrete deposits, also referred to as "spots", of a specific compound such as a protein or a nucleotide sequence attached to a solid substrate.

Each microarray comprises the following sets of spots:
(i) one or more capture spots ("the analyte capture matrix"), each capture spot containing a probe that binds specifically to a target analyte in a test sample; and
(ii) a plurality of calibration spots ("the calibration matrix"), each calibration spot containing a predetermined amount of target analyte, such that each calibration spot corresponds to a known (theoretical) concentration of calibration standard. As noted above, the known concentration of target analyte for a given calibration spot is actually a theoretical value, as an unknown quantity of the target analyte may have been lost during the printing of the calibration spot, and during application and removal of assay reagents. The term "predetermined amount", as used herein, refers to the amount of the calibration standard as calculated based on the known concentration of the spotting buffer comprising the calibration standard and the known volume of the spotting buffer printed on the reaction vessel. The identity of the calibration standard will depend on the nature of the target analyte. The calibration standard may be the target analyte itself in which case, the calibration standard and the reference standard would be the same. In such embodiments, the microarray will comprise a separate calibration standard for each target analyte. Alternatively, the microarray may comprise a single calibration matrix having calibration spots containing each of the target analytes. In alternate embodiments, the calibration standard is a surrogate compound. For example, if the target analyte is an antibody, an appropriate surrogate compound that may be used for the calibration standard may be a different antibody, but of the same class of immunoglobulin as the target antibody. In such embodiments, only one calibration matrix may be required.

In the method according to FIG. 1, there is provided a plurality of microarrays, wherein each microarray is printed on a surface of a discrete reaction substrate. The discrete reaction substrate may be in the form of a bead or a multi-well assay plate with each individual well having one or more microarrays printed thereon. In a preferred embodiment, the method is carried out using a multi-well assay plate suitable for microarray printing thereon. Within each microarray, the number of analyte capture matrices and calibration matrices will depend on the number of target analytes and the nature of the target analytes.

A separate reaction substrate is provided for each test sample to be assayed and for each reference standard. As used herein, the term "reference standard" refers to a solution comprising a known amount of the target analyte, such as a commercially available standard solution of a biomolecule. Where possible, the reference standard is a standard which is established to be equivalent and traceable to an internationally recognised standard which is appropriate for use in the present assay, and has been proven to be stable prior to its stated expiration date. For a given target analyte, the number of reference standards at different concentrations may range between 3 to 16 and more preferably from 5 to 8. The reference standards may be in the form of a linear dilution series with the concentrations falling within the dynamic range of the detection system used to read the microarray.

In the first stage of the method (FIG. 1, Stage 1), a test sample containing an unknown concentration of the target analyte is applied to one of the reaction substrates comprising a microarray as described above (FIGS. 1, (a1) and (b1)). Also, two or more reference standard(s), each containing a known concentration of the target analyte, is each applied to the remaining reaction substrate(s), each reaction substrate comprising a set of spots (i) and (ii) as described above (FIGS. 1, (a2) and (b2)). For the test sample and each of the reference standards, there is also provided a reporting system that provides a signal intensity may be detected and measured ("the measured signal intensity"). The measured signal intensity varies in direct proportion relative to the amount of target analyte or calibration standard that is present in any given spot on the microarray. An example of a suitable reporting system is a fluorescently labelled antibody that binds specifically to the target analyte, wherein the intensity of fluorescence may be measured and is proportional to the amount of bound antibody.

Following application of the test sample and the one or more reference standards to the discrete substrate surfaces of the microarray, the measured signal intensities for the set of calibration spots from each substrate (y axis) is plotted against the respective theoretical concentrations of the calibration spots (x axis). Regression analysis and/or other well-known mathematical and statistical methods are used to prepare a standard curve that best fits the data points, thus forming an initial calibration curve. Thus, there is a first initial calibration curve derived from the calibration spots exposed to the test sample (FIG. 1, (c1)), and a second initial calibration curve derived from the calibration spots exposed to the reference standard (FIG. 1, (c2)).

Next, the "analyte equivalent concentration" ("AEC") is determined by plotting the measured signal intensity of the capture spot(s) on each substrate as a y value on the respective initial calibration curve, finding the corresponding x value (the x axis being in units of concentration), and thus determining the concentration of the target analyte in the test sample (FIG. 1, (d1)), and in the reference standard (FIG. 1, (d2)). Doing so provides the following values:

(1) a first analyte equivalent concentration for a target analyte of unknown concentration in a test sample ("AEC1"; FIG. 1, (e1)); and (2) a second analyte equivalent concentration for each of the one or more reference standards of the target analyte of known concentration ("AEC2"; FIG. 1, (e2)).

It should be noted the analyte equivalent concentration values AEC1 and AEC2 as obtained in this first stage of the method, do not take into account deviations and variations in assay kinetics nor minor inter-lot variations between microarrays, such as may occur during the printing of the capture and calibration spots and during application and removal of assay reagents.

In the second stage of the method (FIG. 1, Stage 2), the analyte equivalent concentrations for the reference standards, AEC2, are plotted against the respective known concentrations of the reference standard ("the reference concentrations"). Regression analysis and/or other well known mathematical and statistical methods are then used to determine a standard curve that best fits the data points, referred to as the "Reference Standardization Curve" (FIG. 1, (f)).

Next, the analyte equivalent concentration for the test sample, AEC 1, is plotted on the Reference Standardization Curve and the corresponding x value for AEC 1 is taken as the corrected target analyte concentration (FIG. 1, (g) and (h), respectively).

Figure 2:
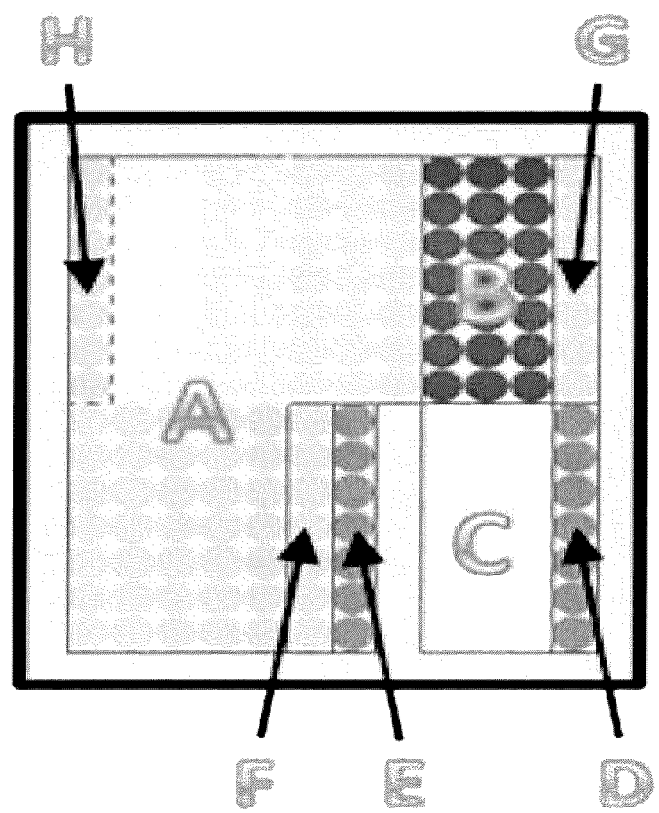
FIG. 2 is a schematic illustration of a multiplex microarray comprising a plurality of spot matrices including: A—calibration matrix; B—first analyte capture matrix; C—second analyte capture matrix; D—positive control matrix for patient sample; E—first analyte positive control matrix; F—negative control matrix; G—a second analyte positive control matrix; and H—a third analyte positive control test matrix.

FIG. 2 illustrates an embodiment, wherein there is provided a microarray useful for quantifying multiple analytes which bind to two different probe compounds. For example, the microarray as illustrated may be useful for quantifying antibodies which bind to two different antigens.

The microarray as illustrated in FIG. 2 comprises a calibration matrix A. The calibration matrix may be printed on the surface of a discrete reaction substrate in the form of a linear, proportional dilution series with the theoretical concentrations of the calibration standard falling within the dynamic range of the detection system used to read the microarray. The number of different concentration levels of the calibration standard may range between 3 and 20 and more preferably from 5 to 12. The calibration matrix may also comprise replicate spots for each of the theoretical concentrations. The number of replicate spots may range between 3 to 15 spots for each concentration level and more preferably between 5 to 8 spots. In the present embodiment as illustrated in FIG. 2, only a single calibration matrix may be required but it will be appreciated that more than one calibration matrices may be included in the microarray. In the present example as illustrated in FIG. 2, the calibration standard may be an antibody different from the target antibodies and which is recognized by further differentially labelled antibody. For example, the calibration standard may be a readily available and inexpensive antibody such as human IgA and human IgM.

The microarray also comprises an analyte capture matrix, which is a subarray of spots comprising an agent (also referred to as a "probe") that selectively binds to the target analyte. In embodiments where the target analyte is a protein, the probe may be an antibody or fragment thereof that binds specifically to the target analyte. Conversely, in embodiments wherein the target analyte is an antibody, the probe may be an antigen specifically bound by the antibody. The microarray may be used to detect and capture antibodies that selectively bind to two different antigens. In the present example as illustrated in FIG. 2, the illustrated microarray comprises analyte capture matrices B and C, made up of analyte capture spots comprising a first and second antigen, respectively.

The total number of replicate spots in the analyte capture matrix is typically at least equal to the total number of replicate spots for each predetermined concentration of the reference standard in the calibration matrix. For example, if the calibration matrix comprises 7 replicate spots for each of the predetermined concentrations of the reference standard, then the sample capture matrix will comprise at least 7 replicate spots for the target analyte.

The microarray may further comprise a positive control matrix for each target analyte. As used herein, the term "positive control matrix" refers to a subarray of spots comprising a conjugate of the target analyte and the agent which selectively binds the target analyte. In use, a signal intensity reading for each positive control matrix confirms that the reporting system (for example, fluorescently labelled antibodies which selectively bind to the target analytes) and the microarray scanner are functioning properly in a given channel. Additionally, signal intensity readings in each of the positive control matrices allows spot finding algorithms such as those of the SQiDworks® Diagnostic Platform laboratory robots (SQI Diagnostics Systems, Inc.) to identify the intensity values for all spots of the microarray for automated analysis.

The microarray illustrated in FIG. 2 comprises a positive control matrix for each type of antibody to be quantified. The IgA positive control matrix H is a subarray of spots comprising an IgA antibody or IgA fragments to verify that the IgA specific labelled reporter and scanner channel of the reporting system are functioning properly. The IgM positive control matrix E is a subarray of spots comprising an IgM antibody or IgM fragments to verify that the IgM specific labelled reporter and scanner channel of the reporting system are functioning. The IgG positive control matrix G is a subarray of spots comprising an IgG antibody or IgG fragments to verify that the IgG specific labelled reporter and scanner channel of the reporting system are functioning.

The microarray may also comprise a negative control matrix F. As used herein, the term "negative control matrix" refers to a subarray of spots which is free of any compound which interacts with a detectable level of any assay analyte or any labelled reporter. In use, a negative signal intensity reading in this region of the microarray confirms that there are no spurious interactions between the differential detectable labels and the microarray.

The microarray may further comprise a sample control matrix D. As used herein, the term "sample control matrix" refers to a subarray of spots comprising an agent which selectively binds to a compound associated with the biological sample. The compound can be a compound naturally occurring in the biological sample with the proviso that the compound is not the same as a target analyte. Alternative, the compound may be a foreign compound added to the biological sample.

Each of the matrices making up the microarray may be printed on the surface of a reaction substrate such as a bead or a well of an assay plate. In a preferred embodiment, the matrices are printed at predetermined X-Y coordinates on the base of a well of an assay plate In the first stage of the method, as described above and as illustrated in FIG. 1, the microarray of FIG. 2 is used to determine the analyte equivalent concentrations of the target analyte in the test sample and in the reference standards.

A predetermined volume of the test sample and of each reference standard is applied to discrete reaction substrates. A separate reaction substrate is used for each test sample and for each reference standard. The target analyte in the test sample and the reference standards are allowed to bind to the probe in the analyte capture spots. The amount of bound analyte is measured using a labelled reporter which selectively binds to the target analyte. The hybridization conditions and choice of labelled reporter will depend on the nature of the target analyte and can be determined using conventional methods. In a preferred embodiment, the reporting system may comprise the use of differentially labelled antibodies which specifically recognize multiple different target analytes.

The signal intensity value corresponding to the amount of the bound labelled reporter in each spot within an microarray is measured using conventional methods. For example, in embodiments directed to the quantification of multiple target analytes, differentially labelled reporters can be used, e.g. fluorescently labelled antibodies which each fluoresce at a different characteristic wavelength. In such embodiments, a charge couple device (CCD) array scanner can be used to measured for the specific fluorescent signal intensity generated by the requisite dye wavelengths emitted by each spot. The scanner generates a multi-color intensity image map of each spot. The intensity of the generated signal is directly proportional to the amount of reporter contained within the printed calibration spots and the amount of analyte from the test sample or reference standard bound to the printed analyte capture spot. For each reaction substrate, measured signal intensity values are obtained for each of the analyte capture spots and for each of the calibration spots.

For each reaction substrate, a calibration curve is generated by fitting a curve to the measured signal intensity values versus the theoretical concentration of the calibration standard as described above in FIGS. 1, (c1 ) and (c2). The analyte equivalent concentration for test sample (AEC1) or for the reference standard (AEC2) is then determined using the initial calibration curve by plotting the measured signal intensity for the test sample or the reference standard on the calibration curve as shown in FIG. 3 (see also FIGS. 1, (d1) and (d2), and relevant description above regarding the same).

Figure 3:
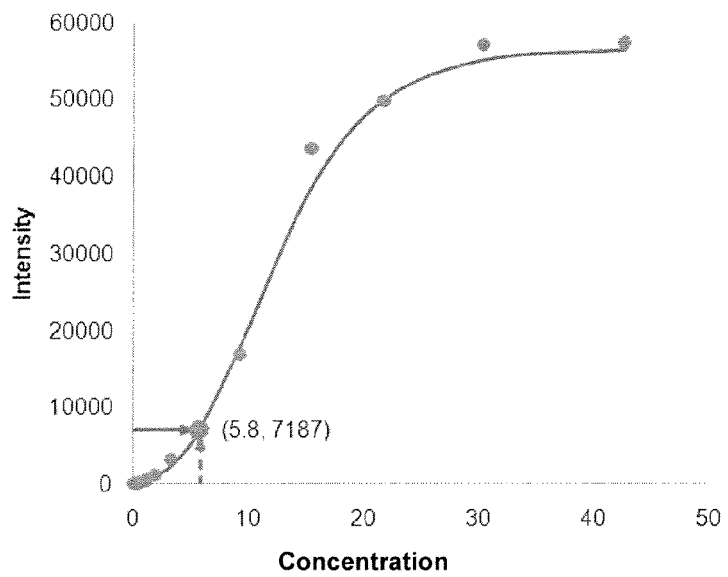
FIG. 3 is an initial calibration curve prepared by plotting normalized measured signal intensities versus the theoretical concentrations of a series of calibration standards at 12 different concentration levels.

FIG. 3 illustrates an initial calibration curve prepared from the results of an assay employing 12 different concentration levels of the calibration standard (denoted in Table 1(a) below as AGM-01 to AGM-12). The measured signal intensity value for each calibration standard (y axis) was plotted against the respective theoretical concentration level of the calibration standard (x axis). The initial calibration curve was then obtained, using well-known methods of regression analysis to fit a curve to the data points. For each of the concentration levels of the calibration standard, the measured intensity value was normalized by identifying the corresponding y value on the calibration curve for each theoretical concentration level (taken as the x value), the corresponding y value being denoted as the "fitted signal intensity".

TABLE 1(a)

Fitted Signal Intensities for a Series of Calibration Spots

| Calibration spot reference number | Theoretical Concentration (x axis) | Fitted signal intensity (y axis) |
| --- | --- | --- |
| AGM-01 | 0.16 | 102 |
| AGM-02 | 0.44 | 207 |
| AGM-03 | 0.73 | 332 |
| AGM-04 | 1.21 | 582 |
| AGM-05 | 2.02 | 1147 |
| AGM-06 | 3.36 | 2576 |
| AGM-07 | 5.6 | 6690 |
| AGM-08 | 9.33 | 18064 |
| AGM-09 | 15.55 | 38573 |
| AGM-10 | 21.77 | 49938 |
| AGM-11 | 30.48 | 55118 |
| AGM-12 | 42.67 | 56369 |

The analyte equivalent concentration for the test sample (AEC1) or for the reference standard (AEC2) may then be determined as follows. The mean value of measured signal intensities of a set of capture spots, taken as the y value, would be plotted on the calibration curve. The corresponding x value would then be the analyte equivalent concentration. As summarized in Table 1(b), for a mean measured signal intensity of 7187 for a given capture spot, a corresponding AEC1 value, calculated from the calibration curve as illustrated in FIG. 3, would be 5.8.

TABLE 1(b)

Calculated AEC1 for a Capture Spot, from the Calibration Curve of FIG. 3

| | Mean Measured Signal Intensity | Calculated AEC1 |
| --- | --- | --- |
| Test Sample (Capture Spot) | 7187 | 5.8 |

In embodiments where the calibration matrix comprises replicate spots for each concentration level of the calibration standard, an initial calibration curve may be generated as follows. The measured intensity signal for each of the replicate spots for a given theoretical concentration of the calibration compound may be normalized to a mean measured intensity signal value, and fitting a curve to the mean measured intensity signal values for each of the theoretical concentrations of the calibration standard, using well-known methods of regression analysis. Similarly, if the analyte capture matrix comprises replicate capture spots, the concentration of the target analyte in the test sample or the reference standard may be determined by normalizing the measured intensity signal value for each of the replicate spots to a mean measured intensity signal value, and calculating the concentration of the target analyte by plotting the mean measured intensity signal value on the calibration curve.

In a preferred embodiment, the normalization of the measured intensity signal value for each of the spots of calibration matrix and the sample capture matrix is performed by applying an algorithm. In yet another preferred embodiment, the algorithm is preferably the Tukey Biweight algorithm, an accepted statistical algorithm which places less emphasis on values as they exist further from the median value of all inclusive replicates (Mosteller, F. and Tukey, J. W. *Data Analysis and Regression: A Second Course in Statistics*; Addison-Wesley: Reading, 1977; pp. 203-209).

The analyte equivalent concentrations for the reference standards (AEC2 values) are used in the second stage of the method to modulate or correct the analyte equivalent concentration for the test sample (AEC1) to provide a more accurate measurement of the amount of target analyte in the test sample (see also FIG. 1, Stage 2 and relevant description above regarding the same). A Reference Standardization Curve is generated by fitting a curve to a graph of the analyte equivalent concentrations for the reference standards (AEC2 values; y axis) versus the known concentrations of the reference standards (x axis). The amount of target analyte in the test sample is then determined by correcting the analyte equivalent concentration. This is accomplished by plotting the analyte equivalent concentration for the test sample (AEC1) on the Reference Standardization Curve, and obtaining the corresponding x value, which is taken as the corrected target analyte concentration. By doing so, this integrates small, random deviations and variations in assay kinetics and minor inter-lot variances between reaction vessels. Thus, the corrected target analyte concentration value is a more accurate quantification of the target analyte.

Figure 4:
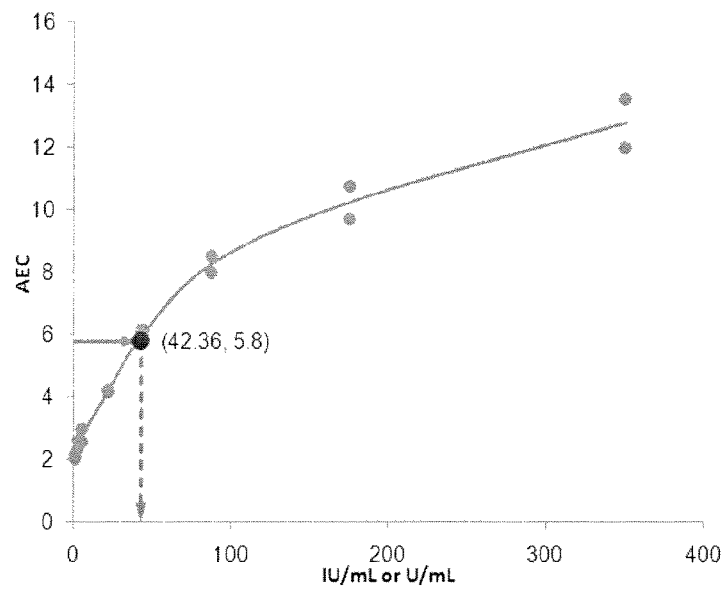
FIG. 4 is a reference standardization curve plotting pairs of replicate analyte equivalent concentration values of a series of calibration standards (AEC2 values) versus known reference standard concentrations expressed as IU/ml or U/ml, and determination of a corrected target analyte concentration from the AEC1 value of a test spot (indicated with the arrows), using the reference standardization curve.

FIG. 4 illustrates the results of an assay employing 8 different concentration levels of the reference standard, each concentration level provided in replicates of two. For each reference standard (denoted in Table 2(a) below as RAS0 to RAS7), its analyte equivalent concentration (AEC2) was determined as discussed above. The analyte equivalent concentrations for each of the reference standards, the AEC2 values (y axis) were plotted against the respective known concentrations of the reference standard (x axis). A curve was then fitted to the data points using well-known methods of regression analysis, thus forming the Reference Standardization Curve as shown in FIG. 4. Each set of AEC2 values for each known concentration level (x value) was then normalized to the corresponding y value on the Reference Standardization Curve, to provide normalized AEC2 values. The normalized AEC2 values and the corresponding known concentration values (x values) noted above are summarized in Table 2(a) below.

TABLE 2(a)

AEC2 Values (Normalized) for a Series of Reference Standards of Known Concentration

| Reference Standard reference number | Known Concentration of Reference Standard (x axis; IU/mL or U/mL) | Normalized AEC2 (y axis) |
|---|---|---|
| RAS0 | 1.4 | 2.0 |
| RAS0 | 1.4 | 1.2 |
| RAS1 | 3.2 | 2.4 |
| RAS1 | 3.2 | 2.6 |
| RAS2 | 5.5 | 2.6 |
| RAS2 | 5.5 | 3.0 |
| RAS3 | 21.9 | 4.2 |
| RAS3 | 21.9 | 4.2 |
| RAS4 | 43.7 | 6.1 |

TABLE 2(a)-continued

AEC2 Values (Normalized) for a Series of Reference Standards of Known Concentration

| Reference Standard reference number | Known Concentration of Reference Standard (x axis; IU/mL or U/mL) | Normalized AEC2 (y axis) |
|---|---|---|
| RAS4 | 43.7 | 5.9 |
| RAS5 | 87.4 | 8.5 |
| RAS5 | 87.4 | 8.0 |
| RAS6 | 174.8 | 10.8 |
| RAS6 | 174.8 | 9.7 |
| RAS7 | 349.6 | 13.5 |
| RAS7 | 349.6 | 12.0 |

The analyte equivalent concentration for the test sample, AEC1=5.8, was then plotted on the Reference Standardization Curve to provide a corrected target analyte concentration of 42.36 (see Table 2(b) below). The corrected target analyte concentration may be expressed as a concentration, i.e. amount per volume (for example: μg/mL; units/mL), or if standardized against a recognized traceable internationally recognized reference calibrator, in International Units (IU) per volume (for example, IU/mL). It is understood that the relevant units of measure will depend on the target analyte to be assayed and whether traceable reference standards were used.

TABLE 2(b)

Calculated Target Analyte Concentration in the Test Sample, Determined from the Reference Standardization Curve of FIG. 4

| | Calculated AEC1 (from Table 1(b)) | Calculated Concentration (IU/mL or U/mL) |
|---|---|---|
| Test Sample (Capture Spot) | 5.8 | 42.36 |

The method disclosed herein can be used to more accurately quantify clinically relevant biomarkers in biological samples for diagnostic or prognostic purposes. For example, the corrected target analyte concentrations for a disease related biomarker can be compared with established index normal levels for that biomarker. Corrected target analyte concentrations levels which exceed index normal levels may be identified as being diagnostic of the disease. The method disclosed herein can also be used to monitor the progress of a disease and also the effect of a treatment on the disease. Levels of a clinically relevant biomarker can be quantified using the disclosed method a plurality of times during a period of treatment. A trending decrease in biomarker levels may be correlated with a positive patient response to treatment.

When the method as disclosed herein is used in a clinical setting, a set of internal quality control rules may be provided for the purposes of evaluating the assay results. These rules can be identified by safety and hazard analysis to mitigate risks such as missing test samples and general failures in the immunochemical reactions. They may include quality control rules for checking fit of calibration and standardization curves, as well as thresholds of controls measuring reporter activity and sample presence. When data is found that does not fit the required control levels or rules, further processing of the data is halted and the value "No Result" may be reported. The internal quality control rules, or invalidation rules, can be present at each level of data processing. For example, the rules may provide for the invalidation of single analyte results where there is a high co-efficient of variance of the replicate capture spots. The rules may provide for the invalidation of results for a given microarray or a given reaction substrate if there is an improper calibration curve or control threshold. The rules may provide the invalidation of a result due to an improper standardization curve.

Further details of the preferred embodiments of the invention are illustrated in the following Example which is understood to be non-limiting with respect to the appended claims.

EXAMPLE 1

Multiplex Microarray for Assaying Rheumatoid Arthritis Biomarkers

Figure 5:
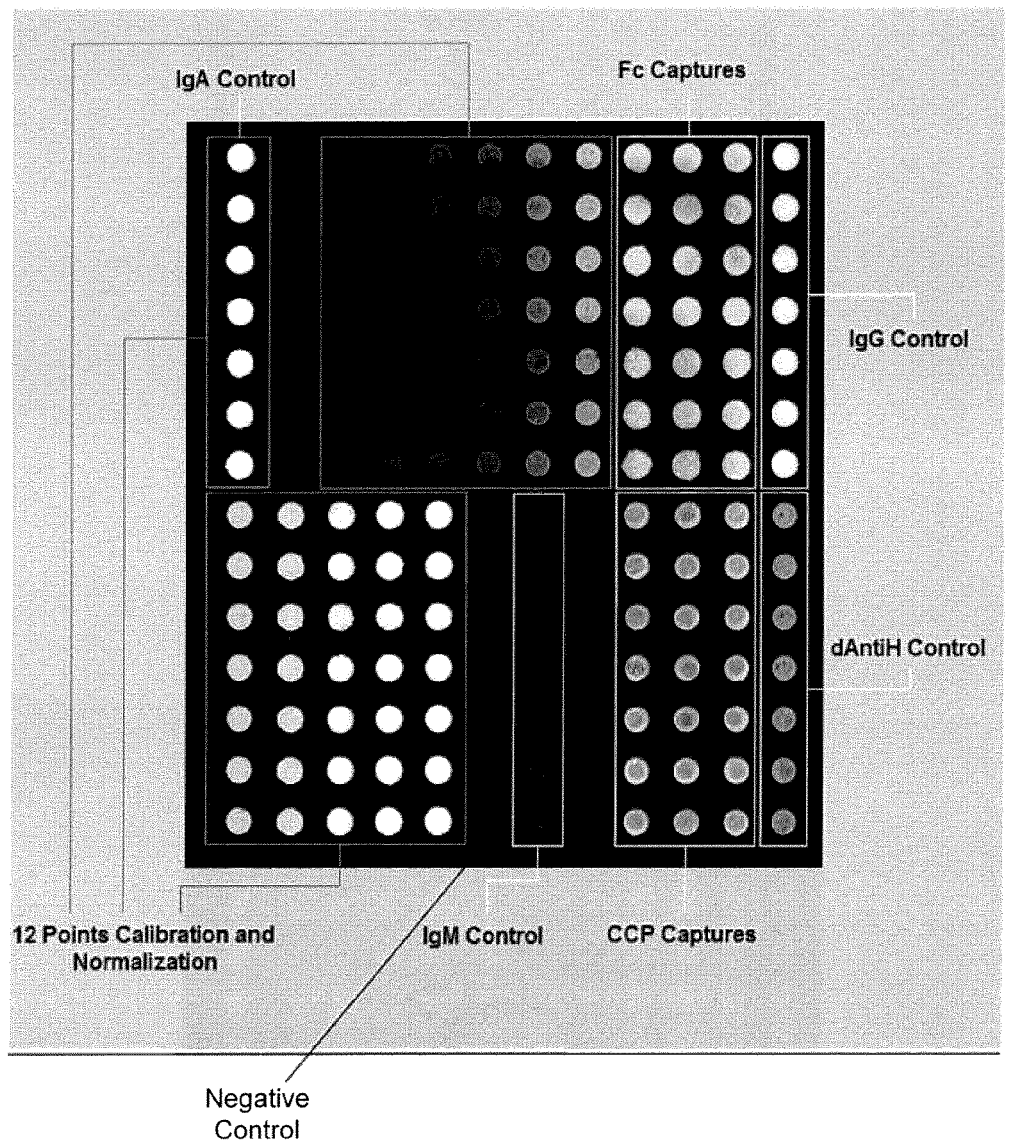
FIG. 5 is a schematic illustration of a multiplex microarray diagnostic assay for rheumatoid arthritis, comprising a series of spot matrices as labelled.

FIG. 5 illustrates a microarray useful for the diagnosing rheumatoid arthritis and for monitoring the effects of treatment in a patient suffering rheumatoid arthritis. The microarray can be used to quantify biomarkers associated with rheumatoid arthritis: rheumatoid factor-IgA (RF-IgA), rheumatoid factor-IgG (RF-IgG), rheumatoid factor-IgM (RF-IgM) and anti-cyclic citrullinated peptide-IgG (CCP-IgG), anti-cyclic citrullinated peptide-IgA (CCP-IgA), and anti-cyclic citrullinated peptide-IgM (CCP-IgM). It was noted that the microarray can be used with a reporting system comprising differentially labelled antibodies which specifically recognize IgA, IgG, and IgM antibodies. The reporter antibodies can be differentially labelled fluorescent antibodies.

The microarray was printed on each well of a 96-well assay plate. The microarray comprised two different sample capture matrices, each capture matrix comprising 21 capture spots. Each capture spot comprised a predetermined relevant amount of rheumatoid factor for capturing RF-IgA, RF-IgG, and RF-IgM and a second analyte capture matrix comprising a predetermined relevant amount of cyclic citrullinated peptide for capturing CCP-IgG, CCP-IgA and/or CCP-IgM. It was noted that the microarray can comprise sample capture matrices for capturing RF-IgA, RF, IgG and RF-IgM and at least one of the anti-cyclic citrullinated peptide antibodies (CCP-IgG, CCP-IgA, and/or CCP-IgM. In the present example, the microarray comprised capture spots for all of the above-noted biomarkers. The microarray also comprised a calibration matrix. The calibration standard was IgG Fab, which is recognized by a IgG reporter antibody. Twelve (12) different concentrations of the calibration standard, spanning a more than 200-fold concentration range, were provided on the microarray. In addition, the calibration matrix comprised 7 replicate spots for each of the 12 different concentration levels.

The microarray further comprised a negative control matrix and a positive control matrix for each of type of antibody to be quantified. The negative control matrix and the positive control matrix each contained 7 replicate spots.

The negative control matrix comprised a plurality of spots which were free of any compound which interacts at a detectable level of any of the assay analytes or any labelled reporter.

The IgA positive control matrix was a subarray of spots comprising an IgA antibody or fragment thereof to verify that the IgA specific labelled reporter and scanner channel of the reporting system were functioning properly. The IgM positive control matrix was a subarray of spots comprising an IgM antibody or fragment thereof to verify that the IgM specific labelled reporter and scanner channel of the reporting system were functioning. The IgG positive control matrix was a subarray of spots comprising an IgG antibody or fragment thereof to verify that the IgG specific labelled reporter and scanner channel of the reporting system are functioning.

The microarray comprised a test control matrix comprising a subarray of spots comprising a donkey anti-human IgM antibody which selectively binds any serum IgM antibodies to confirm a test sample was added to the reaction vessel during the assay.

World Health Organization 64/2 British $1^{st}$ reference preparation of rheumatoid arthritis serum was used as the reference standard for the assay, at 12 different known concentrations (Anderson, S. G. et al. "International reference preparation of rheumatoid arthritis serum." *Bull. World Health Org.* 1970, v. 42, pp. 311-318).

The assay was conducted by applying a predetermined volume (100 microliters, µL) of a patient's serum sample to an individual reaction well of the multi-well assay plate. Prior to application to the reaction well, the test sample was combined with the IgA, IgG, and IgM specific reporter antibodies. The test sample was reacted with the reporter antibodies for approximately 2 minutes and was then dispensed into the reaction well. Typically, there were at least 2 replicate wells for each patient sample. Each of the reference standards were similarly reacted with the reporter antibodies and were applied to individual reaction wells in the assay plate. Typically, there were at least 2 replicate wells for each reference standard. For each of the reaction wells, a multi-coloured intensity image map was generated for each spot of the microarray contained in each of the reaction wells.

For each multi-well assay plate, the assay plate comprised one or more confidence confirmation normalization standards and controls including:

each of 72 of 96 assay wells per assay plate containing at least one positive control for each of RF-IgA, RF-IgG, and RF-IgM;

each of 72 of 96 assay wells per assay plate containing at least one positive control for CCP-IgG, CCP-IgA and/or CCP-IgM;

each of 72 of 96 assay wells per assay plate containing at least one negative control for each of RF-IgA, RF-IgG, RF-IgM, and at least one of CCP-IgG, CCP-IgA and/or CCP-IgM;

each of 72 of 96 assay wells per assay plate containing at least one positive control for each of the traceable reference standards for RF-IgA, RF-IgG, RF-IgM, and at least one of CCP-IgG, CCP-IgA and/or CCP-IgM;

each of 92 of 96 assay wells per assay plate containing one or more configuration controls for confirming matrix location; matrix rotation; matrix shift, and number of spots per array;

each of 92 of 96 assay wells per assay plate containing one or more replicate controls for confirming replicate signal intensity;

each of 92 of 96 assay wells per assay plate containing one or more process controls for serum confirmation; background signal and liquid volume transfer confirmations;

each of 92 of 96 assay wells per assay plate containing one or more configuration controls for confirming internal calibration curves; and each of 92 of 96 assay wells per assay plate containing one or more configuration controls for confirming standardization curves.

For each concentration level of the calibration standard, the measured signal intensities of each the replicate calibrations were normalized by applying the Tukey Biweight algorithm to provide a mean measured signal intensity value for reach concentration level. An initial calibration curve was generated by fitting a curve to the mean measured signal intensity values for each of the concentrations of the calibration standard.

For each of the IgA, IgG, and IgM detection channels, the measured signal intensities for each of the analyte capture spots was normalized by applying the Tukey Biweight algorithm to provide a mean measured signal intensity value which was proportional to the amount of IgA, IgG, or IgM present in the test sample or the reference standard. The mean measured signal intensity value was plotted on the initial calibration curve to provide the analyte equivalent concentrations for each of RF-IgA, RF-IgG, RF-IgM and at least one of CCP-IgG, CCP-IgA and CCP-IgM in the test samples and in the reference standards.

For each of RF-IgA, RF-IgG, RF-IgM and at least one of CCP-IgG, CCP-IgA and CCP-IgM, a Reference Standardization Curve was generated. Each of the standardization curves was generated by fitting a curve to the analyte equivalent concentration values for each of the concentrations of the reference standard (AEC2 values). The analyte equivalent concentrations for each of RF-IgA, RF-IgG, RF-IgM and at least of CCP-IgG CCP-IgA and CCP-IgM in the test samples (AEC1 values) were corrected by plotting the appropriate analyte equivalent concentration value on the Reference Standardization Curve to provide a corrected target analyte concentration for each of the above-noted biomarkers.

Figure 6:
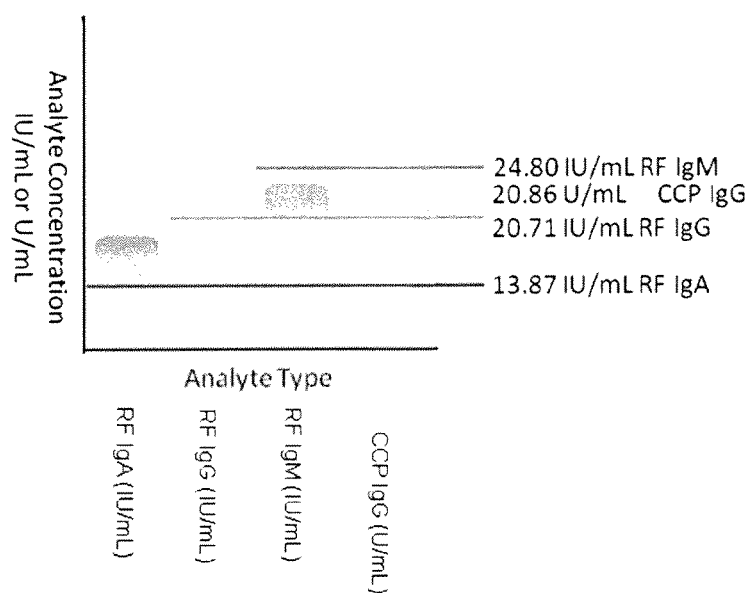
FIG. 6 is a bar graph illustrating measured rheumatoid factor-IgA (RF-IgA), rheumatoid factor-IgG (RF-IgG), rheumatoid factor-IgM (RF-IgM) and anti-cyclic citrullinated peptide-IgG (CCP-IgG) levels and their respective clinical cut-off values.

The resulting corrected concentrations could then be compared to the index normal levels for each of the biomarkers, i.e. the clinically relevant cut off values for the diagnosis of rheumatoid arthritis. In FIG. 6, a bar graph illustrates measured rheumatoid factor-IgA (RF-IgA), rheumatoid factor-IgG (RF-IgG), rheumatoid factor-IgM (RF-IgM) and anti-cyclic citrullinated peptide-IgG (CCP-IgG) levels and their respective clinical cut-off values. Measured levels of the biomarkers that were found to be above the normal levels for each of the biomarkers were identified as being diagnostic for rheumatoid arthritis.

In view of the results obtained, it was concluded that the measurement of the rheumatoid arthritis biomarker levels may be used to monitor the effect of treatment by measuring the biomarker levels a plurality of times during a treatment period.

Although the invention has been described with reference to illustrative embodiments, it is to be understood that the invention is not limited to these precise embodiments. Numerous modifications, variations, and adaptations may be made to the particular embodiments of the invention described above without departing from the scope of the invention, which is defined in the following claims.

We claim:

1. A method of quantifying one or more analytes in a test sample comprising:
    (a) providing a plurality of discrete reaction substrates, each discrete reaction substrate having a microarray printed thereon, said microarray comprising:
        a calibration matrix comprising a plurality of calibration spots, each calibration spot comprising a predetermined amount of a calibration compound, wherein each calibration spot corresponds to a theoretical concentration of the calibration compound; and
        an analyte capture matrix comprising a plurality of capture spots, each capture spot comprising a predetermined amount of an agent which selectively binds to said one or more analytes;
    (b) applying a predetermined volume of the test sample to one of said discrete reaction substrates;
    (c) providing a plurality of reference standards each having a known concentration and each comprising a predetermined amount of each of said one or more analytes;
    (d) applying a predetermined volume of each reference standard to one of said discrete reaction substrates such that said predetermined volume of each reference standard is applied to a microarray that is different from the microarray of the discrete reaction substrate of (b);
    (e) on each discrete reaction substrate from (b) and (d):
        (i) applying a labelled reporter compound, wherein said labelled reporter compound provides a measurable signal intensity that is directly proportional to the amount of the one or more analytes or the calibration compound bound to each spot;
        (ii) measuring a signal intensity value for each spot within the microarray;
        (iii) generating from the calibration matrix a first calibration curve between the theoretical concentration of the calibration compound and the signal intensity measured for the test sample, and generating from the calibration matrix a second calibration curve between the theoretical concentration of the calibration compound and the signal intensity measured for the plurality of the reference standards, in each case said first and second calibration curves being prepared by fitting a curve to a graph of the signal intensity values versus the theoretical concentrations of the calibration compound;
        (iv) determining a first analyte equivalent concentration of the test sample by plotting the signal intensity of the test sample to the first calibration curve, and determining a second analyte equivalent concentration of each of the reference standards by plotting the signal intensity of each of the reference standards to the second calibration curve;
    (f) generating a reference standardization curve by fitting a curve to a graph of the second analyte equivalent concentration versus the known concentration of each of the reference standards; and
    (g) obtaining a corrected analyte concentration by plotting and normalizing the first analyte equivalent concentration of the test sample to the reference standardization curve to obtain a corrected analyte concentration.

2. The method according to claim 1, wherein when the calibration matrix comprises two or more calibration spots that are replicates corresponding to a common theoretical concentration of the calibration compound, in (e(iii)), the first and second calibration curves are generated by:
    normalizing the signal intensity value for each of the replicate calibration spots to a mean signal intensity value for each of said calibration spots; and
    fitting a curve to a graph of the mean signal intensity values for each of said calibration spots versus each of the corresponding theoretical concentrations of a corresponding calibration standard.

3. The method of claim 2, wherein normalization of the measured signal intensity value for each of the spots of calibration matrix and the sample capture matrix is performed by applying Tukey Biweight algorithm.

4. The method according to claim 1, wherein the total number of microarrays of the analyte capture matrix is at least equal to the total number of microarrays of the calibration matrix.

5. The method according to claim 4, wherein there is between 3 to 20 different theoretical concentrations of said analyte corresponding to a linear dilution series and wherein there is between 3 to 15 spots for each of the theoretical concentrations of a calibration standard.

6. The method according to claim 1, wherein the labelled reporter compound is a fluorescently labelled antibody.

7. The method according to claim 1, wherein the plurality of reaction substrates is in the form of a multi-well assay plate.

8. The method according to claim 1, wherein the test sample is a biological sample.

9. A method of quantifying one or more analytes in a test sample comprising:
  (a) providing a plurality of discrete reaction substrates, each discrete reaction substrate having a microarray printed thereon, said microarray comprising:
    a calibration matrix comprising a plurality of calibration spots, each calibration spot comprising a predetermined amount of a calibration compound, wherein each calibration spot corresponds to a theoretical concentration of the calibration compound; and
    an analyte capture matrix comprising a plurality of capture spots, each capture spot comprising a predetermined amount of an agent which selectively binds to said one or more analytes,
    wherein two or more of the capture spots are replicates;
  (b) applying a predetermined volume of the test sample to one of said discrete reaction substrates;
  (c) providing a plurality of reference standards each having a known concentration and each comprising a predetermined amount of each of said one or more analytes;
  (d) applying a predetermined volume of each reference standard to one of said discrete reaction substrates such that said predetermined volume of each reference standard is applied to a microarray that is different from the microarray of the discrete reaction substrate of (b);
  (e) on each discrete reaction substrate from (b) and (d):
    (i) applying a labelled reporter compound, wherein said labelled reporter compound provides a measurable signal intensity that is directly proportional to the amount of the one or more analytes or the calibration compound bound to each spot;
    (ii) measuring a signal intensity value for each spot within the microarray;
    (iii) generating from the calibration matrix a first calibration curve between the theoretical concentration of the calibration compound and the signal intensity measured for the test sample, and generating from the calibration matrix a second calibration curve between the theoretical concentration of the calibration compound and the signal intensity measures for the plurality of the reference standards, in each case said first and second calibration curves being prepared by fitting a curve to a graph of the signal intensity values versus the theoretical concentrations of the calibration compound;
    (iv) determining a first analyte equivalent concentration of the test sample by plotting the signal intensity of the test sample to the first calibration curve, and determining a second analyte equivalent concentration of each of the reference standards by plotting the signal intensity of each of the reference standards to the second calibration curve;
    normalizing the signal intensity value for each of the replicate capture spots to a mean signal intensity value and normalizing the signal intensity value for each of the spots to a mean signal intensity value for each of said capture spots;
    calculating the concentration of the analyte in said test sample, using the mean signal intensity value for each of said capture spots of the reaction substrate of (b) and the first calibration curve; and
    calculating the concentration of the analyte in each said reference standards, using the mean signal intensity values for each of said capture spots of the reaction substrate of (d) and the second calibration curve;
  (f) generating a reference standardization curve by fitting a curve to a graph of the second analyte equivalent concentration versus the known concentration of each of the reference standards; and
  (g) obtaining a corrected analyte concentration by plotting and normalizing the first analyte equivalent concentration of the test sample to the reference standardization curve to obtain a corrected analyte concentration.

* * * * *